United States Patent
Pauly et al.

(10) Patent No.: US 7,651,692 B2
(45) Date of Patent: Jan. 26, 2010

(54) **USE OF EXTRACTS OF THE PLANT *LITCHI CHINENSIS* SONN**

(75) Inventors: Gilles Pauly, Nancy (FR); Louis Danoux, Saulxures les Nancy (FR); Florence Henry, Villers-les-Nancy (FR)

(73) Assignee: Cognis France S.A., Saint-Martory (FR)

( * ) Notice: Subject to any disclaimer, the term of this patent is extended or adjusted under 35 U.S.C. 154(b) by 462 days.

(21) Appl. No.: 10/473,725

(22) PCT Filed: Mar. 27, 2002

(86) PCT No.: PCT/EP02/03426

§ 371 (c)(1),
(2), (4) Date: Oct. 1, 2003

(87) PCT Pub. No.: WO02/080949

PCT Pub. Date: Oct. 17, 2002

(65) Prior Publication Data

US 2004/0101508 A1 May 27, 2004

(30) Foreign Application Priority Data

Apr. 3, 2001 (EP) .................................. 01400844

(51) Int. Cl.
*A61K 8/02* (2006.01)
*A61K 36/00* (2006.01)
*A61Q 9/00* (2006.01)

(52) U.S. Cl. ...................... 424/401; 424/725; 424/777; 424/70.1

(58) Field of Classification Search ................ 424/401, 424/70.1, 725, 777
See application file for complete search history.

(56) References Cited

U.S. PATENT DOCUMENTS

| 4,172,887 | A | | 10/1979 | Vanlerberghe et al. |
| 5,587,171 | A | * | 12/1996 | N'Guyen .................... 424/401 |
| 5,705,169 | A | | 1/1998 | Stein et al. |
| 5,730,960 | A | | 3/1998 | Stein et al. |
| 5,945,091 | A | | 8/1999 | Habeck et al. |
| 6,193,960 | B1 | | 2/2001 | Metzger et al. |

FOREIGN PATENT DOCUMENTS

| DE | 1 165 574 | | 8/1960 |
| DE | 2 024 051 | | 12/1971 |
| DE | 197 12 033 A1 | | 9/1998 |
| DE | 197 56 377 A1 | | 6/1999 |
| EP | 0 693 471 B1 | | 1/1996 |
| EP | 0 694 521 B1 | | 1/1998 |
| EP | 0 818 450 A1 | | 1/1998 |
| FR | 2 252 840 A | | 6/1975 |
| GB | 0 962 919 | | 7/1964 |
| GB | 1 333 475 | | 10/1973 |
| JP | 04 247008 | | 9/1992 |
| JP | 04 247009 | | 9/1992 |
| JP | 2000 128730 | | 5/2000 |
| JP | 2000-128730 | * | 5/2000 |
| JP | 2001-220344 A | | 8/2001 |

OTHER PUBLICATIONS

P.Finkel, "Formulierung kosmetischer Sonnenschutzmittel", SÖFW-Journal, 122, (1996), pp. 543-546, and 548.
P.Finkel, "Formulierung kosmetischer Sonnenschutzmittel",Parfümerie und Kosmetik,80,(1999),pp. 10-12,14-16.
J. Falbe, "Surfactants in Consumer Products", Springer-Verlag, Berlin, 1987, pp. 54-124.
J. Falbe, "Katalysatoren, Tenside und Mineralöladditive", Thieme Verlag, Stuttgart, 1978, pp. 123-217.
Lochhead et al., "Encyclopedia of Polymers and Thickeners", Cosmetics & Toiletries, vol. 108,(1993), pp. 95-114, 116-124, 127-130, 132-135.
Todd et al., "Volatile silicone fluids for cosmetic formulations", Cosmetics & Toiletries, vol. 91,(1976), pp. 29-32.
Kosmetikverordnung, Appendix 6, Parts A and B.
"Kosmetische Färbemittel", Farbstoffkommission der Deutschen Forschungsgemeinschaft, Verlag Chemie, Weinheim, (1984), pp. 81-106.
Porter et al., "The Conversion of Procyanidins and prodelphindins to Cyanidin and Delphindin", Phytochemistry, vol. 25(1), (1986), pp. 223-230.
Vasseur et al., "Appréciation de la Cytotoxicité par la mesure de L'A.T.P.", Journal Francais Hydrologie, (1981), 9, pp. 149-156.
Marion M. Bradford, "A Rapid and Sensitive Method for the Quantitation of Microgram Quantities of Protein Utilizing the Principle of Protein-Dye Binding," Analytical Biochemistry (1976), 72, pp. 248-254.
Knight et al., "A novel coumarin-labelled peptide for sensitive continuous assays of the matrix metalloproteinases", FEBS Letter, (1992), pp. 263-266.
Sami-Manchado et al., "Phenolic Composition of Litchi Fruit Perfcarp", J. Agric. Food Chem., vol. 48, No. 12, (2000), pp. 5995-6002, XP-002259112.

* cited by examiner

*Primary Examiner*—San-ming Hui

(57) ABSTRACT

A cosmetic and/or pharmaceutical composition containing an extract from a pericarp of a *Litchi chinensis* Sonn. plant, and wherein the composition is used to protect human skin and/or hair from environmental influences and ageing.

14 Claims, No Drawings

USE OF EXTRACTS OF THE PLANT *LITCHI CHINENSIS* SONN

BACKGROUND OF THE INVENTION

This application is a 371 of PCT/EP02/03426 filed Mar. 27, 2002.

This invention relates generally to care preparations and, more particularly, to preparations containing extracts from the pericarp of the plant *Litchi chinensis* Sonn. and procyanidins (procyanidolic oligomers) and procyanidin derivatives isolated therefrom and to the use of extracts from the pericarp of the plant *Litchi chinensis* Sonn. and procyanidolic oligomers (OPCs) and derivatives thereof isolated therefrom.

Cosmetic preparations are available to the consumer is a variety of combinations. Not only are these cosmetics expected to have a certain care effect or to eliminate a certain deficiency, there is also an increasing demand for products which have several properties at one and the same time and which therefore show an improved performance spectrum. The user is also entitled to expect the composition of the product to have optimal dermatological compatibility so that even people with sensitive skin do not react with irritation. In addition, however, the preparations should also perform other functions which increasingly lie in the field of care and particularly the protection of skin and hair.

Extracts of plants and their ingredients are being increasingly used in cosmetology and dermatology. Plant extracts have been used for many years in various cultures for medicinal and even cosmetic purposes.

Thus, JP 4247009 describes a mixture of two plant extracts from the fruit of *Litchi chinensis* Sonn. and the whole plant parts of *Ganoderma lucidum* Karst. which were extracted using a water-soluble organic solvent. The composition obtained is used as a skin whitener and moisturizer.

DESCRIPTION OF THE INVENTION

The problem addressed by the present invention was to provide extracts from renewable raw materials for cosmetic and/or dermatological application which would be able to be used in cosmetic or even pharmaceutical preparations and which, besides care properties, would above all have improved protective properties for human skin and/or hair, for example against UV radiation and other environmental influences, and at the same time a preventive and healing effect on manifestations of skin ageing and which could be used as anti-inflammatory agents.

Another problem addressed by the present invention was to provide preparations which would contain active ingredients from renewable raw materials and which, at the same time, could be widely used as care components in cosmetic and skin-care and hair-care products.

These multiple applications of the preparations according to the invention from the renewable raw material of the pericarp of the plant *Litchi chinensis* Sonn. (hereinafter referred to as lychee extract) make it very attractive for the market and the consumer alike. Accordingly, the complex problem addressed by the present invention has been solved by the use of an extract of the pericarp of the plant *Litchi chinensis* Sonn. An extract containing flavone derivatives has proved to be preferred and an OPC-containing extract to be particularly preferred. The OPCs present therein are preferably derivatized to increase stability.

Plants in the context of the present invention are understood to include both whole plants and plant parts (leaves, roots, flowers) and mixtures thereof.

*Litchi chinesis* Sonn.

The extracts to be used in accordance with the invention are obtained from plants of the Sapindaceae family, more particularly the species *Litchi chinensis* Sonn. Litchis are slow-growing trees with a grey trunk which, under good conditions, can reach a height of up to 10 meters. The leaves are leathery and relatively thick. New leaves are initially reddish but gradually change color to lush green. The small yellow-green flowers form long, often upright panicles. Their home is in Southern China although the plants are now cultivated worldwide.

The ripe fruit has a dark red/brown rough surface and is 2.5 to 4 cm in size. Under the fragile pericarp, it has shimmering white fruit flesh with a sweet taste and a jelly-like but firm consistency. The seed of the litchi makes up a significant proportion of the fruit as a whole and is chestnut-brown in color.

Extraction

The extracts to be used in accordance with the invention are produced by conventional methods for extracting plants or plant parts. Fresh or dried plants or plant parts may be used as the starting material although plants and/or plant parts mechanically size-reduced and optionally defatted before extraction are normally used. The pericarp of the plant is particularly preferred for extraction.

Preferred solvents for the extractions are organic solvents, water or mixtures of organic solvents and water, more particularly low molecular weight alcohols, esters, ethers, ketones or halogenated hydrocarbons with more or less large water contents (distilled or nondistilled), preferably aqueous alcoholic solutions with more or less large water contents. Extraction with methanol, water, ethanol and mixtures thereof is particularly preferred. The extraction process is generally carried out at 20 to 100° C., preferably at 30 to 90° C. and more particularly at 40 to 60° C. In one possible embodiment, the extraction process is carried out in an inert gas atmosphere to avoid oxidation of the active principles of the extract. The extraction times are selected by the expert in dependence upon the starting material, the extraction process, the extraction temperature and the ratio of solvent to raw material, etc. After the extraction process, the crude extracts obtained may optionaly be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of dried plants or dried plant parts (optionally defatted) are in the range from 5 to 20% by weight. The present invention includes the observation that the extraction conditions and the yields of the final extracts may be selected by the expert according to the desired application. If desired, the extracts may then be subjected, for example, to spray drying or freeze drying.

The quantity of plant extracts used in the preparations mentioned is determined by the concentration of the individual ingredients and by the type of application envisaged for the extracts. The total quantity of plant extract present in the preparations according to the invention is generally from 0.001 to 25% by weight, preferably from 0.01 to 5% by weight and more particularly from 0.05 to 1.5% by weight, based on the final preparation, with the proviso that the quantities mentioned add up to 100% by weight with water and optionally other auxiliaries and additives.

The extracts according to the invention have an active component content in the extracts of 5 to 100% by weight, preferably 10 to 95% by weight and more particularly 20 to 80% by weight. The active component content in the context of the invention is the sum total of all the active components present in the extract, based on the dry weight of the extract.

Active component in the context of the invention relates to the ingredients present in the extract even though their content and identity cannot yet be determined by conventional methods known to the expert. In addition, active components in the context of the invention are understood to be any ingredients present in the extract of which the effect is already known or of which the effect cannot yet be determined by conventional methods known to the expert.

Active substance in the context of the invention relates to the percentage of substances and auxiliaries/additives present in the preparation except for the water additionally introduced. The total percentage content of auxiliaries/additives can be from 1 to 50% by weight and is preferably from 5 to 40% by weight, based on the final form of the cosmetic and/or dermatological preparations. The preparations are produced by standard cold or hot methods and preferably by the phase inversion temperature method.

Extracts

The extracts according to the invention of the pericarp of the plant *Litchi chinensis* Sonn. generally contain ingredients from the group consisting of flavone derivatives, more particularly flavonols, anthocyanines and flavonols.

Flavone derivatives in the context of the invention are those which can be isolated from the plant *Litchi chinensis* Sonn. More particularly, they are substances which are hydrogenation, oxidation or substitution products of 2-phenyl-4H-1-benzopyran; hydrogenation may already be present in the 2,3-position of the carbon chain, oxidation may already be present in the 4-position and substitution products are understood to be compounds in which one or more hydrogen atoms is/are replaced by hydroxy or methoxy groups. Accordingly, this definition of the flavone derivatives also encompasses such compounds as flavans, flavan-3-ols (catechols, catechol oligomers), flavan-3,4-diols (leucoanthocyanidins), flavones, flavonols and flavonones and derivatives thereof.

Particularly preferred flavone derivatives isolated from the pericarp of the plant *Litchi chinensis* Sonn. are the procyanidolic oligomers (OPCs). These are oligomers of 2 to 8 monomer units of catechol and/or epicatechol. The proanthocyanidolic oligomers (OPCs) are rated for their vitamin P activity.

To increase their stability in formulations, the OPCs are preferably derivatized after extraction and the derivatives obtained are used in the formulations. The esters with OPCs are particularly preferred in this regard.

The present invention relates to the use of extracts of the pericarp of the plant *Litchi chinensis* Sonn. as skin-care and/or hair-care agents. Extracts containing flavone derivatives are preferred for this purposes and OPC-containing extracts particularly preferred. The stability of the OPCs can have been increased by derivatization. The nature of the use encompasses both cosmetically and pharmaceutically active agents.

Care Agents

Care agents in the context of the invention are understood to be skin-care and hair-care agents. These care agents include inter alia a cleaning and restoring effect on skin and hair. They may be applied both topically and orally in the form of tablets, coated pills, capsules, syrups, solutions and granules.

In addition, the preparations according to the invention have an excellent skin-care effect coupled with high dermatological compatibility. The preparations have a number of cosmetic and pharmaceutical effects. Accordingly, the present invention also relates to the use of extracts from the pericarp of the plant *Litchi chinensis* Sonn, preferably extracts containing flavone derivatives and more particularly OPC-containing extracts

- as sun protection factors; more particularly against UV-A radiation and/or against UV-B radiation;
- against free radicals;
- as antioxidants;
- as anti-inflammatory agents, particularly for inhibiting the harmful effects of respiratory burst caused by the penetration of polymorphonuclear leucocytes in stressed skin;
- as anti-ageing preparations for skin;
- as a protease inhibitor, more particularly as a plasmin (serine protease) inhibitor and/or as an MMP and/or collagenase and/or elastase inhibitor.

In the context of the invention, respiratory burst is understood to be the activation of leucocytes, more particularly polymorphonuclear neutrophilic granulocytes. Cutaneous inflammation can be caused by UV-B radiation stimulating epidermal keratinocytes. Acute leucocyte infiltration then sets in. Such activation of these leucocytes, more particularly polymorphonuclear neutrophilic granulocytes, is known as respiratory burst and can lead to tissue destruction by released reactive oxygen radicals (reactive oxygen species—ROS) and by lysosomal enzymes.

Sun or UV Protection Factors

According to the invention, the extracts from the pericarp of the plant *Litchi chinensis* Sonn. act as sun protection factors. The extracts containing flavone derivatives are preferred and the extracts containing OPCs or derivatives thereof particularly preferred.

Sun protection factors or UV protection factors in the context of the invention are light protection factors which are useful in protecting human skin against harmful effects of direct and indirect solar radiation. The ultraviolet radiation of the sun responsible for tanning of the skin is divided into the sections UV-C (wavelengths 200-280 nm), UV-B (280-315 nm) and UV-A (315-400 nm).

The pigmenting of normal skin under the influence of solar radiation, i.e. the formation of melanins, is differently effected by UV-B and UV-A. Exposure to UV-A (long-wave UV) results in darkening of the melanins already present in the epidermis without any sign of harmful effects. It is different with so-called short-wave UV (UV-B). This promotes the formation of so-called late pigment through the reformation of melanins. However, before the (protective) pigment is formed, the skin is exposed to the unfiltered radiation which, depending on the exposure time, can lead to reddening of the skin (erythema), inflammation of the skin (sunburn) or even blisters.

Extracts from the pericarp of the plant *Litchi chinensis* Sonn. may additionally be present in combination with sun protection factors or UV protection factors which, as UV absorbers or light filters, convert the UV radiation ito harmless heat.

These other UV protection factors are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives as described in EP 0694521 B1.

Suitable water-soluble substances are
- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 1-phenyl-3-(4'-isopropylphenyl)-propane-1,3-dione and the enamine compounds described in DE 19712033 A1 (BASF). The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or dimethicones. So-called micro- or nanopigments are preferably used in sun protection products. Micronized zinc oxide is preferably used. Other suitable UV filters can be found in P. Finkel's review in SÖFW-Journal 122, 543 (1996) and in Parfümerie und Kosmetik 3 (1999), pages 11 et seq.

According to the invention, the extracts from the pericarp of the plant *Litchi chinensis* Sonn. are active against fibroblast and/or keratinocyte damage by UV-A radiation and/or UV-B radiation.

UV-A rays penetrate into the dermis where they lead to oxidative stress which is demonstrated by lipoperoxidation of the cytoplasm membranes. The lipoperoxides are degraded to malonaldialdehyde (MDA) which will crosslink many biological molecules, such as proteins and nuclein bases (enzyme inhibition or mutagenesis). The extracts from the pericarp of the plant *Litchi chinensis* Sonn. according to the invention significantly reduce the level of MDA in human fibroblasts induced by UV-A rays and thus show a high capacity for reducing the harmful effects of oxidative stress on the skin.

UV-B rays initiate inflammation by activating an enzyme, namely phospholipase A2 or PLA2. This inflammation (erythema, odema) is indued by the removal of arachidonic acid from the phospholipids of the plasma membrane by the phospholipase. Arachidonic acid is the precursor of the prostaglandins which cause inflammation and cell membrane damage. The prostaglandins E2 (=PGE2) are formed by cyclooxygenase. The degree of release of the cytoplasm enzyme LDH (lactate dehydrogenase) in human keratinocytes serves as a marker for cell damage.

The extracts from the pericarp of the plant *Litchi chinensis* Sonn. according to the invention reduce the effect of UV-B radiation on the number of keratinocytes and on the content of released LDH. Accordingly, the extracts have the ability to reduce cell membrane damage caused by UV-B radiation.

According to the invention, the extracts from the pericarp of the plant *Litchi chinensis* Sonn., preferably the extracts containing flavone derivatives and more particularly the extracts containing OPCs and/or OPC derivatives act as antioxidants or radical traps.

Antioxidants in the context of the invention are oxidation inhibitors which can be isolated from the pericarp of the plant *Litchi chinensis* Sonn. Antioxidants are capable of inhibiting or preventing unwanted changes caused by the effects of oxygen and other oxidative processes in the substances to be protected. The effect of antioxidants consists mainly in their acting as radical traps for the free radicals occurring during autoxidation.

Besides the use of extracts from the pericarp of the plant *Litchi chinensis* Sonn. as antioxidants, other already known antioxidants may also be used. One possible use of the antioxidants, for example in cosmetic and/or dermopharmaceutical preparations, is their use as secondary sun protection factors because antioxidants are capable of interrupting the photochemical reaction chain which is initiated when UV rays penetrate into the skin. Besides the plant extract according to the invention, typical examples are amino acids (for example glycine, alanine, arginine, serine, threonine, histidine, tyrosine, tryptophane) and derivatives thereof, imidazoles (for example urocanic acid) and derivatives thereof, peptides, such as D,L-carnosine, D-carnosine, L-camosine and derivatives thereof (for example anserine), carotinoids, carotenes (for example α-carotene, β-carotene, lycopene, lutein) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, boldin, boldo extract, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

The other UV protection factors or antioxidants may be added in quantities of 0.01 to 25, preferably 0.03 to 10 and more particularly 0.1 to 5% by weight, based on the total quantity in the preparations.

According to the invention, the extracts from the pericarp of the plant *Litchi chinensis* Sonn., preferably the extracts containing flavone derivatives and more particularly the extracts containing OPCs and OPC derivatives act as anti-inflammatory care agents which can cure or prevent inflammation of the skin. The inflammation can be caused by a variety of factors. More particularly, inflammation induced by UV radiation or skin contamination or bacterially and hormonally induced changes in the skin, for example acne, can be treated.

According to the invention, the extracts from the pericarp of the plant *Litchi chinensis* Sonn., preferably the extracts containing flavone derivatives and more particularly the extracts containing OPCs and OPC derivatives are active against ageing of the skin, more particularly against any form of wrinkling or lining. Care agents of this type are also known as anti-ageing preparations. The uses include the slowing down of skin ageing processes. Ageing of the skin can be caused by a variety of factors, more particularly by apoptosis, by UV radiation or by the destruction of the skin's own proteins, such as for example collagen- or elastin-induced skin damage. The extracts from the pericarp of the plant *Litchi chinensis* Sonn. according to the invention act as protease inhibitors and more particularly as plasmin and/or MMP and/ or collagenase and/or elastase inhibitors. MMP are the initials for matrix metalloproteases.

In principle, the use of the extracts according to the invention as a protective and restoring care agent is possible for any preparations that are used to prevent damage or in the event of damage to the skin and/or hair and hence in skin and hair care. Another use in this field comprises application to sensitive skin damaged by allergies or other causes. The skin damage can be caused by a variety of factors.

The preparations according to the invention may be used for the production of cosmetic and/or dermatological preparations such as, for example, foam baths, shower baths, creams, gels, lotions, alcoholic and aqueous/alcoholic solutions, emulsions, wax/fat compounds, stick preparations, powders or ointments. These preparations may also contain mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, perservatives, perfume oils, dyes and the like as further auxiliaries and additives.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic formulations from DE 2024051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types

[Goodrich]; Synthalens® [Sigma]; Keltrol types [Kelco]; Sepigel types [Seppic]; Salcare types [Allied Colloids]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil. 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Biogenic Agents

Biogenic agents in the context of the invention also include those which do not come from the plant *Cassia alata* such as, for example, tocopherol acetate, tocopherol palmitate, ascorbic acid, (deoxy)ribonucleic acid and fragmentation products thereof, retinol, bisabolol, allantoin, phytantriol, panthenol, AHA acids, amino acids, ceramides, pseudoceramides, essential oils, plant extracts and additional vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

- astringent active principles,
- oil components,
- nonionic emulsifiers,
- co-emulsifiers,
- consistency factors,
- auxiliaries in the form of, for example, thickeners or complexing agents and/or
- non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol,
- sugars containing 5 to 12 carbon atoms, for example glucose or sucrose;
- amino sugars, for example glucamine;
- dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic fragrances. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

EXAMPLES

Example 1

Extraction of an OPC- and Flavonoid-Rich Extract 1,000 ml methanol were added to 100 g powdered litchi shells in a glass beaker and stirred for one hour at 50° C. After the residue had been filtered and washed with 100 ml methanol, the methanol of the combined extracts was distilled off and the dry residue was taken up in 100 ml distilled water. After centrifuging in a Cryofuge 6000 (15 mins. at 4,200 r.p.m.), the aqueous solution was extracted four times with 100 ml ethyl acetate. The organic phase was dried over 15 g sodium sulfate and the ethyl acetate was evaporated. The residue was again taken up in distilled water and extracted four times with 100 ml ethyl acetate. After the ethyl acetate had been distilled off, the aqueous solution was freeze-dried. The yield came to 6.13 g. The OPC content of the extract obtained was determined by the method of Porter et al. in Phytochemistry 25(1), pp. 223-230, 1996: The conversion of procyanidins and prodelphindins to cyanidin and delphindin. The quantity of OPC in g, based on 100 extract, amounted to 19.98%.

Example 2

Extraction of a Rutin- and Anthocyan-Rich Extract 1,000 ml methanol were added to 100 g powdered litchi shells in a glass beaker and stirred for one hour at 50° C. After the residue had been filtered and washed with 100 ml methanol, the methanol of the combined extracts was distilled off and the dry residue was taken up in 100 ml distilled water. After centrifuging in a Cryofuge 6000 (15 mins. at 4,200 r.p.m.), the aqueous solution was freeze-dried.

Example 3

Cell Protecting Effect Against UV-A on Human Fibroblasts Cultivated In Vitro

Background: UV-A rays penetrate into the dermis where they lead to oxidative stress which is demonstrated by lipoperoxidation of the cytoplasm membranes.

The lipoperoxides are degraded to malonaldialdehyde (MDA) which will crosslink many biological molecules, such as proteins and nuclein bases (enzyme inhibition or mutagenesis).

Method: To carry out these tests, a defined culture medium containing the fibroblasts is inoculated with foetal calf serum and added to the plant extract (in the defined medium containing 10% fetal calf serum) 72 hours after inoculation.

After incubation for 48 hours at 37° C./5% $CO_2$, the culture medium was replaced by saline solution (physiological NaCl solution) and the fibroblasts were exposed to a dose of UV-A (365 nm, 20 $J/cm^2$; tubes: MAZDA FLUOR TFWN40).

After the exposure to UV-A, the MDA level (malonaldialdehyde level) in the supernatant sodium chloride solution was quantitatively determined by reaction with thiobarbituric acid.

TABLE 1 exposure of human fibroblasts to UV-A (20 $J/cm^2$) in vitro

| UV-A (20 $J/cm^2$) | Levels in % by comparison with the control | | |
|---|---|---|---|
| | MDA released | Cell proteins | GSH/protein |
| Control (not exposed) | 0 | 100 | 100 |
| No addition | 100 | 101 | 73 |
| 0.001% extract of Example 1 | 57 | 99 | 101 |

TABLE 1-continued exposure of human fibroblasts to UV-A (20 J/cm²) in vitro

| UV-A (20 J/cm²) | MDA released | Cell proteins | GSH/protein |
|---|---|---|---|
| 0.003% extract of Example 1 | 31 | 105 | 87 |
| 0.01% extract of Example 1 | 7 | 106 | 99 |
| 0.001% extract of Example 2 | 75 | 98 | 102 |
| 0.003% extract of Example 2 | 48 | 105 | 81 |
| 0.01% extract of Example 2 | 25 | 106 | 72 |
| 0.0003% tocopherol | 11 | 97 | 78 |

Levels in % by comparison with the control

The exposure to UV-A resulted in a considerable increase in the outpouring of MDA whereas the intracellular GSH level was reduced by ca. 27%. Addition to the litchi pericarp extracts reduces the amount of MDA released and keeps the GSH level high.

Example 4

Cell Protecting Effect Against UV-B in Human Keratinocytes Cultivated In Vitro

Background: UV-B rays cause inflammation (erythema, edema) by activating an enzyme, namely phospholipase A2 or PLA2, which removes arachidonic acid from the phospholipids of the plasma membranes. Arachidonic acid is the precursor of the prostaglandins which cause inflammation and cell membrane damage; the prostaglandins E2 (=PGE2) are formed by cyclooxygenase.

Method: The effect of UV-B radiation was investigated in vitro in keratinocytes by determining the release of the cytoplasm enzyme LDH (lactate dehydrogenase). This enzyme serves as a marker for cell damage.

To carry out the tests, a defined medium containing fetal calf serum was inoculated with the keratinocytes and the plant extract (diluted with saline solution) was added 72 hours after the inoculation.

The keratinocytes were then exposed to a dose of UV-B (50 mJ/cm²-tubes: DUKE FL40E).

After incubation for another day at 37° C./5% $CO_2$, the LDH content in the supernatant was determined. The LDH (lactate dehydrogenase) content was determined by an enzyme reaction (kit used to determine LDH levels from Roche). The number of adhering keratinocytes was determined (after trypsin treatment) with a particle counter.

TABLE 2 cell protecting effect of litchi pericarp extracts against UV-B rays

| UV-B (50 mJ/cm²) | No. of keratinocytes | LDH released |
|---|---|---|
| Control (not exposed) | 100 | 0 |
| No addition | 33 | 100 |
| 0.0001% extract of Example 1 | 37 | 90 |
| 0.0003% extract of Example 1 | 35 | 94 |
| 0.001% extract of Example 1 | 36 | 64 |
| 0.0003% extract of Example 2 | 36 | 87 |
| 0.001% extract of Example 2 | 35 | 84 |
| 0.003% extract of Example 2 | 34 | 73 |
| 0.001% aspirin | 33 | 68 |

Levels in % by comparison with the control

The exposure to UV-B induced an increase in the LDH level whereas the number of viable keratinocytes fell by 67%. When the litchi pericarp extract was added, the quantity of LDH released was reduced by up to 25%.

Example 5

Activity Towards Free Radicals

The effectiveness of the extracts against oxidative stress was investigated in a first series of tests. The extracts of Examples 1 and 2 were used.

The first test substrate selected was diphenyl picryl hydrazyl (DPPH), a purple-red colored stable radical which changes into its colorless leuco derivative on contact with radical trappers. The change of color can be followed photometrically. The test results are set out in Table 3 (DPPH Test). In another test, the hydroxylation of salicylic acid by hydroxyl radicals (from the reaction of hydrogen peroxide with iron(III) ions and EDTA) was investigated as a reference system. This reaction can also be photometrically investigated because the hydroxylation product is reddish in color. The influence of the extracts on the formation of hydroxysalicylic acid was measured at an optical density of 490 nm. The results are also set out in Table 3. In a third and final test, xanthine oxidase was selected as the test system. Under oxidative tress, the enzyme converts purine bases, for example adenine or guanine, into uronic acid. The oxygen radicals intermediately formed can be detected by reaction with luminol (via the luminescence) and quantitatively determined. The luminescence output diminishes in the presence of substances with radical-trapping properties. These results are set out in Table 4 where the inhibition is again shown in %-absolute (Luminol Test).

TABLE 3 chemical tests

| EC50 in % | Litchi pericarp extract of Example 1 | Litchi pericarp extract of Example 2 | Tocopherol | Ascorbic acid |
|---|---|---|---|---|
| DPPH Test | 0.001% | 0.0085% | 0.0067% | 0.0013% |
| Fenton's reaction | No effect | 0.077% | Not available | 0.1% |

TABLE 4 biochemical tests

| EC50 in % | Litchi pericarp extract of Example 1 | Litchi pericarp extract of Example 2 | Tocopherol | Ascorbic acid |
|---|---|---|---|---|
| Luminol | 0.00006% | 0.00069% | No effect up to 1% | 0.0006% |
| Luminol + microperoxydase | 0.00361% | 0.02048% | No effect up to 1% | 0.0058% |
| NBT | 0.00836% | 0.04969% | No effect up to 1% | 0.5909% |

Example 6

Skin Regenerating and Revitalizing Activity

The object of this test is to demonstrate the regenerating and revitalizing activity of litchi pericarp extracts on human fibroblast cultures in vitro.

Human fibroblasts were inoculated with 10% by weight fetal calf serum in a defined nutrient medium (DMEM=Dulbecco Minimum Essential Medium, a product of Life Technologie S.a.r.l.) and incubated for 24 h at 37° C. in a 5% $CO_2$ atmosphere. The nutrient medium containing fetal calf serum was then replaced by a nutrient medium of DMEM without fetal calf serum. Active substance in the form of the two extracts of the pericarp of *Litchi chinensis* Sonn. was then added to this nutrient medium in various concentrations. After the fibroblasts had been incubated for 3 days in the nutrient medium, growth and metabolic activity were evaluated by determining the intracellular ATP content by Vasseur's method (Journal Français Hydrologie, 1981, 9, 149-156) and the protein content by Bradford's method (Anal. Biochem. 1976, 72, 248-254).

TABLE 5 toxicity test on human fibroblasts

| $LD_{50}$ in % (w/v) | Litchi pericarp extract of Example 1 | Litchi pericarp extract of Example 2 | Tocopherol | Ascorbic acid |
|---|---|---|---|---|
| Proteins | 0.015 | 0.023 | Not toxic up to 0.01 | 0.0055 |
| ATP | 0.005 | 0.019 | Nt toxic up to 0.01 | 0.0056 |

Neither litchi pericarp extract improved the cell metabolism.

Example 7

Inhibition of Elastase Activity

Serine proteases, such as elastase for example, degrade elastin, proteoglycans and collagen and thus weaken the connective tissue. The following test was conducted to investigate the inhibiting properties of the extract of Example 1 on a chromogenic synthetic substrate (marked with Congo Red). The incubation time was 30 mins. at room temperature. The inhibition was followed photometrically at 410 nm; 1'α1-antitrypsin was used as positive standard. The results are set out in Table 6.

TABLE 6 extract of Example 1

| Test substance | Concentration in % (w/v) | Elastase inhibition in % |
|---|---|---|
| Litchi extract of Example 1 | 3 | 60 |
| Litchi extract of Example 1 | 2 | 27 |
| 1'α1-Antitrypsin | 0.1 | 68 |

A 3% extract from the pericarps of *Litchi chinensis* Sonn. according to the invention is capable of inhibiting elastase activity almost as much as the natural inhibitor antitrypsin.

Example 8

Inhibition of Collagenase Activity

After exposure to the sun, dermal fibroblasts of elderly people pour out collagenases—also known as matrix metalloprotease (MMP). The following test was conducted to investigate the inhibiting properties of the extract of Example 1 on a synthetic substrate MCA-Pro-Leu-Gly-Leu-DPA-Ala-Arg-$NH_2$ (Knight er al., 1992, FEBS Letter, 296, pp. 263-266) and human MMP-1. The incubation time was 60 mins. at room temperature. The hydrolysis of the substrate was determined by fluorescence spectrometry at $\lambda_{em}$=393 nm ($\lambda_{ex}$=328 nm). The metalloprotease TIMP-1 (MMP inhibitor occurring naturally in tissue) was used as the comparison standard. The results are set out in Table 7.

TABLE 7 extract of Example 1

| Test substance | Concentration in % (w/v) | MMP-1 Inhibition in % |
|---|---|---|
| Litchi extract of Example 1 | 0.1 | 95 |
| Litchi extract of Example 1 | 0.05 | 71 |
| Litchi extract of Example 1 | 0.015 | 33 |
| Litchi extract of Example 1 | 0.005 | 13 |
| TIMP-1 | 50 nmol | 93 |

A 0.1% extract from the pericarps of *Litchi chinensis* Sonn. according to the invention is capable of inhibiting collagenase activity almost as much as the natural inhibitor TIMP-1.

Example 9

Inhibition of Collagenase Synthesis

This test is used to evaluate the ability of the litchi extract to reduce the toxic effects of UV-A radiation on human fibroblasts cultivated in vitro. To this end, both the quantity of the enzyme MMP-1 (matrix metalloproteinase) poured out and the quantity of the natural enzyme inhibitor TIMP-1 are determined. UV-A radiation is used in this test because it can penetrate into the dermis and induce oxidative stress which leads to ageing of the skin.

To this end, the fibroblasts are cultivated in a precisely defined medium containing fetal calf serum. The litchi extract of Example 1 is added 2 to 3 days after inoculation. After further incubation for one day at 37° C./5% $CO_2$, the culture medium is replaced by a salt solution and the fibroblasts are exposed to UV-A (15 J/cm$^2$, lamp: SOL500, Dr. Höhnle. filter: H1, radiometer: Vibert Lourmat). After the exposure, the fibroblasts are incubated for another two days. The MMO-1 and TIMP-1 contents of the supernatant medium are determined with an Amersham test kit (Kit No. RPN2610 and RPN2611). No extract was added to the control. The results are set out in Table 8.

TABLE 8

MMP-1 and TIMP-1 poured out after exposure to UV-A

| | Without exposure to UV-A | | After exposure to UV-A | |
|---|---|---|---|---|
| Substance added | Value | Standard deviation | Value | Standard deviation |
| | MMP-1 poured out in ng/ml | | | |
| Control | 49 | 9 | 199 | 25 |
| Dexamethasone 0.1 μm | 2 | 0 | 7 | 3 |
| 0.0006% litchi extract of Example 1 | 60 | 20 | 140 | 17 |
| 0.003% litchi extract of Example 1 | 82 | 11 | 164 | 8 |

TABLE 8-continued

MMP-1 and TIMP-1 poured out after exposure to UV-A

| Substance added | Without exposure to UV-A | | After exposure to UV-A | |
|---|---|---|---|---|
| | Value | Standard deviation | Value | Standard deviation |
| TIMP-1 poured out in ng/ml | | | | |
| Control | 50 | 4 | 28 | 3 |
| Dexamethasone | 39 | 1 | 19 | 3 |
| 0.0006% litchi extract of Example 1 | 53 | 1 | 15 | 2 |
| 0.003% litchi extract of Example 1 | 56 | 2 | 15 | 3 |
| 0.006% litchi extract of Example 1 | 50 | 1 | 12 | 2 |

The quantity of MMP-1 poured out after exposure to UV-A radiation is distinctly reduced.

Example 10

Inhibition of Plasmin

Background: Plasmin is a human serine protease which has a crucial role in the wound healing process. It dissolves inter alia small fibrin clots and supports the release of keratinocytes which contribute to the healing process.

Plasminogen is the proenzyme which is activated to plasmin by the protease urokinase. Urokinase is secreted by activated keratinocytes during the healing of wounds and in the event of dermal irritation or cutaneous inflammation. It was shown that the expression and the secretion of urokinase are induced by the influence of UV-B radiation on the skin and that the proenzyme plasminogen can be found near the extracellular matrix.

In addition, plasmin is capable of activating pro-MMP3 which contributes towards the reduction of dermal glycoproteins and proteoglycans. Accordingly, plasmin has an important role in skin ageing processes and more particularly in photoinduced ageing processes of human skin.

Method: Human plasmin was mixed with the extract of Example 1 and incubated for 5 mins. at 20° C. Thereafter, either synthetic substrate, especially "Val-Leu-paranitroanilide", a product of Chromogenix, or natural pro-MMP3 obtained from Merck-Eurolab was added to the mixture. In the case of the synthetic substrate, absorption at 405 nm was measured every 5 minutes over a period of 30 minutes and the release of paranitroanilines was thus determined. In a second series of tests, enzymatic activity was demonstrated by the Western Blot method after incubation for 6 hours at 37° C.

The inhibition of enzymatic activity was tested against a control with no substrate and against a reference substance, more particularly Aprotinine, a product of Sigma.

TABLE 9 plasmin inhibition after addition of the synthetic substrate

| Litchi extract of Example 1 [µg/ml] | % Inhibition compared with the control |
|---|---|
| 0 | 0 |
| 2.5 | 0 |
| 5 | 55 |

TABLE 9-continued plasmin inhibition after addition of the synthetic substrate

| Litchi extract of Example 1 [µg/ml] | % Inhibition compared with the control |
|---|---|
| 10 | 65 |
| 25 | 83 |
| 50 | 90 |
| 100 | 94 |
| Aprotinine: 50 µg/ml | 100 |

A concentration of 4.5 µg/ml of the litchi extract of Example 1 produces 50% inhibition.

TABLE 10 inhibition of the activation of pro-MMP3 by plasmin

| | Pro-MMP3 content |
|---|---|
| Control without plasmin | 49260 |
| Control with plasmin | 1435 |
| Litchi extract of Example 1 - 0.003% | 1117 |
| Litchi extract of Example 1 - 0.03% | 44641 |

6. Anti-Inflammatory activity

Background: Cutaneous inflammation can be produced by UV-B radiation through the stimulation of epidermal keratinocytes. This is followed by the onset of acute leucocyte infiltration.

This activation of the leucocytes, especially neutrophilic granulocytes, is known as respiratory burst and can lead to tissue destruction by reactive oxygen radicals released (reactive oxygen species—ROS) and by lyosomal enzymes.

Method: Anti-inflammatory activity was studied on a cell line of human leucocytes (neutrophilic granulocytes). To this end, the cells were incubated with various concentrations of extracts of Example 1 to be tested, after which a respiratory burst was induced by yeast cell extract ("zymosan") by activation of the cells for 30 mins. with 0.1 ml zymosan. The content of oxygen radicals intermediately formed was determined for 60 seconds by reaction with luminol via the luminescence and quantitatively evaluated. The luminescence yield falls in the presence of substances with radical-trapping properties. The results are set out in Table 4. The percentage of released radicals was determined against a reference substance (Minocycline—a radical trapper). The results are expressed in % relative to the control. For control purposes, the number of intact cells was determined with a particle counter and is shown in % by comparison with the control.

TABLE 11 determination of the released oxygen radicals

| Substance | Concentration % by weight | ROS content (%/control) | No. of intact cells |
|---|---|---|---|
| Control | | 100 | 100 |
| Minocycline (Sigma) 0.001% | | 28 | 100 |
| Extract of Example 1 | 0.0001 | 92 | 99 |
| | 0.001 | 25 | 96 |

It can be seen from the above results that the extracts of Example 1 according to the invention have a strong anti-inflammatory effect in a concentration of 0.001%.

Exemplary Formulations of Cosmetic Preparations

The extracts obtained in accordance with Example 1 were used in the following formulations according to the invention. The cosmetic preparations thus produced showed very good skin-care properties in relation to comparison formulations C1, C2 and C3 coupled with good dermatological compatibility. The preparations according to the invention are also stable to oxidative decomposition.

TABLE 12

Soft cream formulations K1 to K7
(All quantities in % by weight, based on the cosmetic preparation)

| INCI name | K1 | K2 | K3 | K4 | K5 | K6 | K7 | C1 |
|---|---|---|---|---|---|---|---|---|
| Glyceryl Stearate (and) Ceteareth-12/20 (and) Cetearyl Alcohol (and) Cetyl Palmitate | 8.0 | 8.0 | 8.0 | 8.0 | 8.0 | 8.0 | 8.0 | 8.0 |
| Cetearyl Alcohol | 2.0 | 2.0 | 2.0 | 2.0 | 2.0 | 2.0 | 2.0 | 2.0 |
| Dicaprylyl Ether | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 3.0 | 3.0 | 3.0 | 3.0 | 3.0 | 3.0 | 3.0 | 3.0 |
| Glycerin (86% by weight) | 3.0 | 3.0 | 3.0 | 3.0 | 3.0 | 3.0 | 3.0 | 3.0 |
| Extract of Example 1 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | | | | to 100 | | | | |

TABLE 13

Night cream formulations K8 to K14
(All quantities in % by weight, based on the cosmetic preparation)

| INCI name | K8 | K9 | K10 | K11 | K12 | K13 | K14 | C2 |
|---|---|---|---|---|---|---|---|---|
| Polyglyceryl-2 Dipolyhydroxystearate | 4.0 | 4.0 | 4.0 | 4.0 | 4.0 | 4.0 | 4.0 | 5.0 |
| Polyglyceryl-3 Diisostearate | 2.0 | 2.0 | 2.0 | 2.0 | 2.0 | 2.0 | 2.0 | 2.0 |
| Cera Alba | 2.0 | 2.0 | 2.0 | 2.0 | 2.0 | 2.0 | 2.0 | 2.0 |
| Zinc Stearate | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 8.0 | 8.0 | 8.0 | 8.0 | 8.0 | 8.0 | 8.0 | 8.0 |
| Dicaprylyl Ether | 5.0 | 5.0 | 5.0 | 5.0 | 5.0 | 5.0 | 5.0 | 5.0 |
| Magnesium sulfate | 1.0 | 1.0 | 1.0 | 1.0 | 1.0 | 1.0 | 1.0 | 1.0 |
| Glycerin (86% by weight) | 5.0 | 5.0 | 5.0 | 5.0 | 5.0 | 5.0 | 5.0 | 5.0 |
| Extract of Example 1 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | | | | to 100 | | | | |

TABLE 14

W/O body lotion formulations K15 to K21.
(All quantities in % by weight, based on the cosmetic preparation)

| INCI name | K15 | K16 | K17 | K18 | K19 | K20 | K21 | C3 |
|---|---|---|---|---|---|---|---|---|
| PEG-7 Hydrogenated Castor Oil | 7.0 | 7.0 | 7.0 | 7.0 | 7.0 | 7.0 | 7.0 | 7.0 |
| Decyl Oleate | 7.0 | 7.0 | 7.0 | 7.0 | 7.0 | 7.0 | 7.0 | 7.0 |
| Cetearyl Isononanoate | 7.0 | 7.0 | 7.0 | 7.0 | 7.0 | 7.0 | 7.0 | 7.0 |
| Glycerin (86% by weight) | 5.0 | 5.0 | 5.0 | 5.0 | 5.0 | 5.0 | 5.0 | 5.0 |
| MgSO$_4$.7H$_2$O | 1.0 | 1.0 | 1.0 | 1.0 | 1.0 | 1.0 | 1.0 | 1.0 |
| Extract of Example 1 | 1.5 | 1.5 | 1.5 | 1.5 | 1.5 | 1.5 | 1.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | | | | to 100 | | | | |

[1] Deoxyribonucleic acid: molecular weight ca. 70,000, purity (determined by spectrophotometric measurement of absorption at 260 nm and 280 nm): at least 1.7

TABLE 15

Cosmetic preparations (all quantities in % by weight, based on the cosmetic preparation; water, preservative to 100% by weight)

| Composition (INCI) | 1 | 2 | 3 | 4 |
|---|---|---|---|---|
| Texapon ® NSO Sodium Laureth Sulfate | 38.0 | 38.0 | 25.0 | — |
| Texapon ® SB3 Disodium Laureth Sulfosuccinate | — | — | 10.0 | — |
| Plantacare ® 818 Coco Glucosides | 7.0 | 7.0 | 6.0 | — |
| Plantacare ® PS 10 Sodium Laureth Sulfate (and) Coco Glucosides | — | — | — | 20.0 |
| Dehyton ® PK 45 Cocamidopropyl Betaine | — | — | 10.0 | — |
| Lamesoft ® PO 65 Coco-Glucoside (and) Glyceryl Oleate | 3.0 | | | 4.0 |
| Lamesoft ® LMG Glyceryl Laurate (and) Potassium Cocoyl Hydrolyzed Collagen | — | 5.0 | — | — |
| Euperlan ® PK 3000 AM Glycol Distearate (and) Laureth-4 (and) Cocamidopropyl Betaine | — | 3.0 | 5.0 | 5.0 |
| Extract of Example 1 | 1.0 | 1.0 | 1.0 | 1.0 |
| Arlypon ® F Laureth-2 | 3.0 | 3.0 | 1.0 | — |
| Sodium Chloride | — | 1.5 | — | 1.5 |

Cosmetic preparations "2-in-1" shower bath (all quantities in % by weight, based on the cosmetic preparation; water, preservative to 100% by weight)

| Composition (INCI) | 5 | 6 | 7 | 8 |
|---|---|---|---|---|
| Texapon ® NSO Sodium Laureth Sulfate | 30.0 | 25.0 | | 25.0 |
| Plantacare ® 818 Coco Glucosides | | | | 8.0 |
| Plantacare ® 2000 Decyl Glucoside | | 8.0 | | |
| Plantacare ® PS 10 Sodium Laureth Sulfate (and) Coco Glucosides | | | 20.0 | |
| Dehyton ® PK 45 Cocamidopropyl Betaine | | | 10.0 | 10.0 |
| Lamesoft ® PO 65 Coco-Glucoside (and) Glyceryl Oleate | 5.0 | | | |
| Lamesoft ® LMG Glyceryl Laurate (and) Potassium Cocoyl Hydrolyzed Collagen | | | 5.0 | 5.0 |

TABLE 15-continued

| Composition (INCI) | | | | | |
|---|---|---|---|---|---|
| Gluadin ® WQ Laurdimonium Hydroxypropyl Hydrolyzed Wheat Protein | 3.0 | | | | |
| Gluadin ® WK Sodium Cocoyl Hydrolyzed Wheat Protein | | | | | |
| Euperlan ® PK 3000 AM Glycol Distearate (and) Laureth-4 (and) Cocamidopropyl Betaine | 5.0 | 3.0 | 4.0 | — | |
| Panthenol | 0.5 | — | — | 0.5 | |
| Extract of Example 1 | 1.0 | 1.0 | 1.0 | 1.0 | |
| Arlypon ® F Laureth-2 | 2.6 | 1.6 | — | 1.0 | |
| Sodium Chloride | — | — | — | — | |

Cosmetic preparations foam bath (all quantities in % by weight, based on the cosmetic preparation; water, preservative to 100% by weight)

| Composition (INCI) | 9 | 10 | 11 | 12 | 13 |
|---|---|---|---|---|---|
| Texapon ® NSO Sodium Laureth Sulfate | — | 30.0 | 30.0 | — | 25.0 |
| Plantacare ® 818 Coco Glucosides | — | 10.0 | — | — | 20.0 |
| Plantacare ® PS 10 Sodium Laureth Sulfate (and) Coco Glucosides | 22.0 | — | 5.0 | 22.0 | — |
| Dehyton ® PK 45 Cocamidopropyl Betaine | 15.0 | 10.0 | 15.0 | 15.0 | 15.0 |
| Monomuls ® 90-O 18 Glyceryl Oleate | 0.5 | | | | |
| Lamesoft ® PO 65 Coco-Glucoside (and) Glyceryl Oleate | | 3.0 | | 3.0 | |
| Cetiol ® HE PEG-7 Glyceryl Cocoate | | | 2.0 | | 2.0 |
| Nutrilan ® I-50 Hydrolyzed Collagen | 5.0 | | | | |
| Gluadin ® W 40 Hydrolyzed Wheat Gluten | | 5.0 | | 5.0 | |
| Gluadin ® WK Sodium Cocoyl Hydrolyzed Wheat Protein | | | 7.0 | | |
| Euperlan ® PK 3000 AM Glycol Distearate (and) Laureth-4 (and) Cocamidopropyl Betaine | 5.0 | — | — | 5.0 | — |
| Arlypon ® F Laureth-2 | | | 1.0 | | |
| Sodium Chloride | 1.0 | | 1.0 | | 2.0 |
| Extract of Example 1 | 1.0 | 1.0 | 1.0 | 1.0 | 1.0 |

Cosmetic preparations (all quantities in % by weight, based on the cosmetic preparation; water, preservative to 100% weight)

| Composition (INCI) | 14 | 15 | 16 | 17 | 18 |
|---|---|---|---|---|---|
| Dehymuls ® PGPH Polyglyceryl-2 Dipolyhydroxystearate | 4.0 | 3.0 | — | 5.0 | — |
| Lameform ® TGI Polyglyceryl-3 Diisostearate | 2.0 | 1.0 | — | — | — |
| Emulgade ® PL 68/50 Cetearyl Glucoside (and) Cetearyl Alcohol | — | — | — | — | 4.0 |
| Eumulgin ® B2 Ceteareth-20 | | | | | |
| Tegocare ® PS Polyglyceryl-3 Methylglucose Distearate | | | 3.0 | | |
| Eumulgin VL 75 Polyglyceryl-2 Dipolyhydroxystearate (and) Lauryl Glucoside (and) Glycerin | | | | | |
| Bees Wax | 3.0 | 2.0 | 5.0 | 2.0 | — |
| Cutina ® GMS Glyceryl Stearate | — | — | — | — | — |
| Lanette ® O Cetearyl Alcohol | — | — | 2.0 | — | 2.0 |
| Antaron ® V 216 PVP/Hexadecene Copolymer | — | — | — | — | — |
| Myritol ® 818 Cocoglycerides | 5.0 | — | 10.0 | — | 8.0 |
| Finsolv ® TN C12/15 Alkyl Benzoate | — | 6.0 | — | 2.0 | — |
| Cetiol ® J 600 Oleyl Erucate | 7.0 | 4.0 | 3.0 | 5.0 | 4.0 |
| Cetiol ® OE Dicaprylyl Ether | 3.0 | — | 6.0 | 8.0 | 6.0 |
| Mineral Oil | — | 4.0 | — | 4.0 | — |
| Cetiol ® PGL Hexadecanol (and) Hexyldecyl Laurate | — | 7.0 | 3.0 | 7.0 | 4.0 |
| Panthenol/Bisabolol | 1.2 | 1.2 | 1.2 | 1.2 | 1.2 |
| Litchi extract (Example 1) | 1.0 | 1.0 | 1.0 | 1.0 | 1.0 |
| Copherol ® F 1300 Tocopherol/Tocopheryl Acetate | 0.5 | 1.0 | 1.0 | 2.0 | 1.0 |
| Neo Heliopan ® Hydro Sodium Phenylbenzimidazole Sulfonate | 3.0 | — | — | 3.0 | — |
| Neo Heliopan ® 303 Octecrylene | — | 5.0 | — | — | — |
| Neo Heliopan ® BB Benzophenone-3 | 1.5 | — | — | 2.0 | 1.5 |
| Neo Heliopan ® E 1000 Isoamyl p-Methoxycinnamate | 5.0 | — | 4.0 | — | 2.0 |
| Neo Heliopan ® AV Octyl Methoxycinnamate | 4.0 | — | 4.0 | 3.0 | 2.0 |
| Uvinul ® T 150 Octyl Triazone | 2.0 | 4.0 | 3.0 | 1.0 | 1.0 |
| Zinc Oxide | — | 6.0 | 6.0 | — | 4.0 |
| Titanium Dioxide | — | — | — | — | — |
| Glycerol (86% by weight) | 5.0 | 5.0 | 5.0 | 5.0 | 5.0 |

Cosmetic preparations (all quantities in % by weight, based on the cosmetic preparation; water, preservative to 100% weight)

| Composition (INCI) | 19 | 20 | 21 | 22 | 23 |
|---|---|---|---|---|---|
| Dehymuls ® PGPH Polyglyceryl-2 Dipolyhydroxystearate | — | — | — | — | — |
| Lameform ® TGI Polyglyceryl-3 Diisostearate | — | — | — | — | — |
| Emulgade ® PL 68/50 Cetearyl Glucoside (and) Cetearyl Alcohol | — | — | — | 3.0 | — |
| Eumulgin ® B2 Ceteareth-20 | — | — | 2.0 | — | — |
| Tegocare ® PS Polyglyceryl-3 Methylglucose Distearate | — | 4.0 | — | — | — |
| Eumulgin VL 75 Polyglyceryl-2 Dipolyhydroxystearate (and) Lauryl Glucoside (and) Glycerin | 3.5 | — | — | 2.5 | — |
| Bees Wax | — | — | — | — | — |
| Cutina ® GMS Glyceryl Stearate | 2.0 | 4.0 | — | — | 4.0 |
| Lanette ® O Cetearyl Alcohol | 4.0 | 2.0 | 4.0 | 4.0 | 1.0 |
| Antaron ® V 216 PVP/Hexadecene Copolymer | 3.0 | — | — | — | 2.0 |
| Myritol ® 818 Cocoglycerides | 6.0 | 6.0 | — | 5.0 | 5.0 |
| Finsolv ® TN C12/15 Alkyl Benzoate | — | 3.0 | — | — | 2.0 |
| Cetiol ® J 600 Oleyl Erucate | 3.0 | 3.0 | — | 5.0 | 4.0 |
| Cetiol ® OE Dicaprylyl Ether | 5.0 | 4.0 | 3.0 | 4.0 | 6.0 |
| Mineral Oil | 2.0 | — | 1.0 | — | — |
| Cetiol ® PGL Hexadecanol (and) Hexyldecyl Laurate | — | — | — | 1.0 | — |
| Panthenol/Bisabolol | 1.2 | 1.2 | 1.2 | 1.2 | 1.2 |
| Litchi extract (Example 1) | 1.0 | 1.0 | 1.0 | 1.0 | 1.0 |
| Copherol ® F 1300 Tocopherol/Tocopheryl Acetate | 1.0 | 1.0 | 2.0 | 0.5 | 2.0 |
| Neo Heliopan ® Hydro Sodium Phenylbenzimidazole Sulfonate | — | 2.0 | — | 2.0 | — |
| Neo Heliopan ® 303 Octecrylene | 4.0 | 5.0 | — | — | 10.0 |
| Neo Heliopan ® BB Benzophenone-3 | — | — | — | 2.0 | — |
| Neo Heliopan ® E 1000 Isoamyl p-Methoxycinnamate | 2.0 | 4.0 | 10.0 | — | — |
| Neo Heliopan ® AV Octyl Methoxycinnamate | 3.0 | 4.0 | — | 10.0 | 2.0 |
| Uvinul ® T 150 Octyl Triazone | 1.0 | 4.0 | 3.0 | 3.0 | 3.0 |

TABLE 15-continued

| | | | | | |
|---|---|---|---|---|---|
| Zinc Oxide | — | — | — | — | 5.0 |
| Titanium Dioxide | — | — | 5.0 | — | — |
| Glycerol (86% by weight) | 5.0 | 5.0 | 5.0 | 5.0 | 5.0 |

(1-2) shower bath, (3) shower gel, (4) wash lotion
(14) w/o sun protection cream, (15-17) w/o sun protection lotion, (18, 21, 23) o/w sun protection lotion, (19, 20, 22) o/w sun protection cream All substances with the registered trade mark symbol ® named and used in Tables 12 to 15 are brands and products of the COGNIS Group.

We claim:

1. A skin and/or hair treating composition comprising:
    (a) at least a first component selected from the group consisting of surfactants, oils, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self tanning agents, tyrosine inhibitors, hydrotropes, solubilizers, preservatives, perfume oils, dyes, and combinations of two or more of these; and
    (b) a neutral extract from a pericarp of a *Litchi chinensis* Sonn. plant, said extracted being present in an amount effective to protect human skin and/or hair from environmental influences and ageing.

2. The composition of claim 1 wherein said extract comprises at least one hydrogenation, oxidation or substitution product of 2-phenyl-4H-1-benzopyran.

3. The composition of claim 1 wherein the extract contains a procyanidolic oligomer.

4. The composition of claim 1 wherein the extract is a neutral methanolic extract.

5. The composition of claim 1 wherein the extract is present in the composition in an amount of from about 0.001 to 25% by weight.

6. The composition of claim 1 wherein the extract is present in the composition in an amount of from about 0.01 to 5% by weight.

7. The composition of claim 1 wherein the extract is present in the composition in an amount of from about 0.05 to 1.5% by weight.

8. A process for protecting human skin and/or hair comprising contacting the skin and/or hair with a composition containing a neutral extract from a pericarp of a *Litchi chinensis* Sonn. plant.

9. The process of claim 8 further containing a hydrogenation, oxidation or substitution product of 2-phenyl-4H-1-benzopyran.

10. The process of claim 8 wherein the extract contains a procyanidolic oligomer.

11. The process of claim 8 wherein the extract is a neutral methanolic extract.

12. The process of claim 8 wherein the extract is present in the composition in an amount of from about 0.01 to 25% by weight.

13. The process of claim 8 wherein the extract is present in the composition in an amount of from about 0.01 to 5% by weight.

14. The process of claim 8 wherein the extract is present in the composition in an amount of from about 0.05 to 1.5% by weight.

* * * * *

UNITED STATES PATENT AND TRADEMARK OFFICE
CERTIFICATE OF CORRECTION

PATENT NO. : 7,651,692 B2
APPLICATION NO. : 10/473725
DATED : January 26, 2010
INVENTOR(S) : Pauly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1130 days.

Signed and Sealed this

Twenty-eighth Day of December, 2010

David J. Kappos
*Director of the United States Patent and Trademark Office*